United States Patent
Kong et al.

(10) Patent No.: US 8,109,184 B2
(45) Date of Patent: Feb. 7, 2012

(54) METHOD AND DEVICE FOR CUTTING FRESH TISSUE SLICES

(76) Inventors: Jian-Qiang Kong, Greenville, NC (US); George Y Kong, Greenville, NC (US)

( * ) Notice: Subject to any disclaimer, the term of this patent is extended or adjusted under 35 U.S.C. 154(b) by 395 days.

(21) Appl. No.: 12/310,519

(22) PCT Filed: May 22, 2007

(86) PCT No.: PCT/US2007/012120
§ 371 (c)(1),
(2), (4) Date: Feb. 27, 2009

(87) PCT Pub. No.: WO2008/030279
PCT Pub. Date: Mar. 13, 2008

(65) Prior Publication Data
US 2010/0175520 A1    Jul. 15, 2010

Related U.S. Application Data

(60) Provisional application No. 60/842,386, filed on Sep. 6, 2006.

(51) Int. Cl.
*G01N 1/06* (2006.01)
*B26D 1/45* (2006.01)
(52) U.S. Cl. .......................... 83/13; 83/646
(58) Field of Classification Search ........... 83/13, 915.5, 83/401, 703, 410, 646, 705, 409.2, 563, 613, 83/638
See application file for complete search history.

(56) References Cited

U.S. PATENT DOCUMENTS

| | | | |
|---|---|---|---|
| 3,828,641 A | 8/1974 | Sitte | |
| 5,181,443 A * | 1/1993 | Sitte et al. | 83/72 |
| 5,226,335 A | 7/1993 | Sitte et al. | |
| 5,865,081 A * | 2/1999 | Myers | 83/149 |
| 5,906,148 A | 5/1999 | Aihara et al. | |
| 6,209,437 B1 * | 4/2001 | Izvoztchikov et al. | 83/707 |
| 6,619,173 B2 | 9/2003 | Bellasalma | |
| 6,651,538 B2 * | 11/2003 | Tamura et al. | 83/575 |
| 7,146,895 B2 | 12/2006 | Kong et al. | |

FOREIGN PATENT DOCUMENTS

JP    57100335 A    6/1982
WO    03/093799 A1    11/2003

OTHER PUBLICATIONS

King, Marcus J., "Slicing frozen meat with oscillating knife." Meat Science, vol. 51, 1999, pp. 251-269.

* cited by examiner

*Primary Examiner* — Ghassem Alie
(74) *Attorney, Agent, or Firm* — Richard C. Litman (57) ABSTRACT

The method and device for cutting fresh tissue slices utilizes a vibrating microtome. The vibrating microtome uses a cutting blade that vibrates in a horizontal direction. The microtome has a base, a specimen holder attached to the base, and a diagonal slide carriage and support arm that are supported on the base for movement diagonally with respect to the specimen holder. A vibrating blade support is located on the support arm and moves horizontally with respect to the specimen holder. A cutting blade is mounted on the vibrating blade support and moves in a compound diagonal and vibrating motion with respect to the specimen holder.

14 Claims, 4 Drawing Sheets

METHOD AND DEVICE FOR CUTTING FRESH TISSUE SLICES

CROSS-REFERENCE TO RELATED APPLICATIONS

This application claims priority, under 35 USC 120, to U.S. provisional patent application No. 60/842,386, filed Sep. 6, 2006, the disclosure of which is expressly incorporated herein by reference.

FIELD OF THE INVENTION

The present invention is directed generally to a vibrating microtome. More specifically, the present invention is directed to a vibrating microtome that utilizes a blade which is movable in two directions. Most specifically, the present invention is directed to a vibrating microtome, and to a method of its use in the preparation of live or fixed tissue slices. The tissue specimens are embedded inside a specimen syringe. A slice thickness is selected using a stepper motor to drive a micrometer. A cutting blade is caused to slide diagonally, and to vibrate horizontally to slice very thin layers or slices off the specimen which is caused to extend from the specimen syringe. The vibrating and sliding blade microtome, in conjunction with the tissue embedding and slice thickness determination provides a much improved tissue slice quality.

BACKGROUND OF THE INVENTION

Microtomes are generally well-known and are typically used in biomedical experiments to prepare thin slices of tissue that can then be subjected to microscopic studies. The tissue to be sliced is often embedded in paraffin or is hardened by freezing so that it can be sliced as thinly as possible, typically through the use of a microtome. Live tissues and freshly fixed tissues are typically too soft for this type of cutting and it is thus difficult to obtain thin slices of such live tissues and freshly fixed tissues. One attempted solution has been the provision of a vibrating blade microtome in which the cutting blade has been vibrated horizontally with respect to the typically vertical or perpendicular movement of the cutting blade edge. Such vibrating microtomes are specifically intended to cut soft tissue slices without the need for tissue embedding or freezing. The horizontal oscillation of the blade, or its oscillation is a direction which is generally parallel to the longitudinal axis of the cutting edge, is provided as a high frequency vibration that has been more effective in slicing soft tissue samples than were prior cut devices. The resultant slices, cut by the vibrating microtomes, have had better slice quality than have slices cut by direct blade chopping.

In all current vibrating microtomes, the blade vibrates generally parallel with respect to the longitudinal axis of the cutting blade. Typically this means that the blade vibrates in a generally horizontal, side to side direction, at a high frequency. An amplitude of such a vibrating stroke must be at least 0.6 mm. If the stroke amplitude is less than this amount, the blade will not cut through the live tissue. Instead, the live tissue or the freshly fixed specimen will merely be compressed and will push back against the horizontally vibrating blade.

Vibrating microtomes have been noted recently as having undesirable vibrations of the cutting blade in the Z-axis direction; i.e. the direction perpendicular to both the X-axis blade vibration direction and the Y-axis cutting direction. Efforts have been made in prior vibrating microtomes to reduce this Z-axis movement of the cutting blade using a so-called "zero —" technique. While the blade movement is most often tested and quantified in test conditions, during vibrating of the blade but without cutting a tissue slice, the Z-axis movement or vibration of the cutting blade in operating conditions has been largely ignored.

Double edged razor blades are widely used in vibrating microtomes for cutting tissue slices. Such a razor blade is broken or separated into two single edge blade parts by being severed or snapped along its longitudinal axis prior to use. The now half blade, with its single cutting edge is clamped, generally at its middle, along its longitudinal axis in the blade holder of a currently available vibrating microtome and is used to cut tissue slices. The thin razor blade is apt to be bent or deflected relative to the blade holder, particularly in the portion of the blade that is unsupported by the blade holder of the vibrating microtome. The razor blade is typically mounted on the blade holder and is inclined at an angle of 15-35 degrees, with respect to the surface of the tissue specimen. During slicing of the specimen, the specimen will itself tend to pull and to bend the blade toward the specimen. Such a bending of the blade, during slicing of the specimens, causes the formation of chatter marks in the cut or sliced specimen because of blade bending, or chatter, in the Z-axis direction. Resistance of the tissue specimen to being sliced, and the inherent thin blade structure, together with its being mounted in a somewhat flexible fashion, all contribute to flexure of the blade in the Z-axis and to the resultant formation of tissue damage by the infliction of chatter marks on the surface of the cut tissue specimens.

In current vibrating machines, the edge of the cutting blade vibrates on a horizontal cutting plane. Such a vibrating motion requires a long vibrating arm so that the cutting blade will be located in the middle of the tissue bath container. This relatively long vibrating arm is heavy and is difficult to support so that it will be able to vibrate at the desired speed but will not wobble.

In U.S. Pat. No. 7,146,895, to Kong et al., the applicants in the subject application, there is disclosed a sliding blade microtome. As described in that patent, the disclosure of which is expressly incorporated herein by reference, a diagonally sliding cutting blade is usable to slice thin specimens of live or dead tissue, which specimens have been embedded in a gel and have been extended from the open end of a specimen-holding syringe, by the use of a sliding blade microtome machine. The sliding blade machine disclosed in this prior Kong patent can cut soft tissue such as brain cerebrum into slices. However, this prior device still has several limitations. A first of these is that in connection with high fiber containing tissue, which thus tends to be difficult to cut, such as brain stem or cerebellum, direct sliding cannot cut through the tough tissue thus resulting in low quality tissue slices. Also, the thinnest slices that can be cut with the sliding blade machine described in the above-identified prior Kong patent have a thickness of about 70 to 80 μm. This thickness of cut precludes the sliding blade machine from being used in histology studies which typically require slice thicknesses between 10 and 40 μm.

It will thus be seen that a need exists for a device for cutting fresh tissue slices and for a method of using such a device that overcomes the limitations of the presently existing procedures and apparatus. The method and device for cutting fresh tissue slices in accordance with the present invention provides such a device and method and is a substantial advance in the art.

SUMMARY OF THE INVENTION

It is an object of the present invention to provide a device for use in cutting fresh tissue slices.

Another object of the present invention is to provide a vibrating blade microtome.

A further object of the present invention is to provide a vibrating sliding-blade microtome.

Yet another object of the present invention is to provide a method for using a vibrating, sliding-blade microtome to reduce tissue damage.

Still a further object of the present invention is to provide a vibrating, sliding-blade microtome that eliminates chattering in a Z-axis direction.

Even yet another object of the present invention is to provide a vibrating, sliding-blade microtome which reduces mechanical trauma on tissue slices.

The method and device for cutting fresh tissue slices, in accordance with the present invention utilizes a vibrating microtome, in which the cutting blade vibrates in a generally horizontal direction, with a sliding blade mechanism that causes the blade to also travel in a diagonal X-Y axis direction. The vibrating sliding-blade microtome in accordance with the present invention also adheres the cutting blade to one surface of a blade holder in a procedure that substantially reduces bending and resultant chattering of the blade in the Z-axis direction. The method and device in accordance with the present invention is particularly intended for use in the slicing of live or fixed tissue slices which are not hard or rigid. Such specimens are not embedded in paraffin and are not frozen. The vibrating sliding-blade microtome in accordance with the present invention cuts specimen slices that have substantially higher numbers of live/dead cell ratios than are capable of being obtained with prior art devices. Such a higher number of live/dead cell ratio is an indication of slice viability.

The vibrating, sliding-blade microtome in accordance with the present invention combines a transverse or back and forth, generally horizontal vibrating motion with a diagonal downward sliding motion. The resultant compound cutting blade movement has a substantial effect on the cutting efficiency of the vibrating sliding-blade microtome of the present invention. Whereas, in the prior art devices, the blade vibration amplitude had to be at least 0.6 mm, in the subject device, that amplitude can be as little as 0.1 mm. The specimen being cut is not compressed by the blade vibrating movement so that the cutting efficiency of the blades is increased, and the mechanical stress imparted to the specimen is reduced.

In contrast with prior art devices, the razor blade, or more typically, the half of a broken double-edged razor blade is glued onto a one piece blade holder. This allows the blade to be securely attached to the blade holder all along its length and at one side of the blade holder. The glue can extend to the edge of the blade holder and thus can extend to within 0.5 mm of the cutting edge of the razor blade. This forms a very rigid, uniform support for the thin razor blade and essentially eliminates blade edge wobble. In clamped blades, there are typically one or more clamping screws or the like. The blade is unevenly stressed and is subjected to blade edge wobble. The elimination of blade edge wobble by the use of the blade mounting through the use of adhesives of the present invention, in combination with the vibrating, sliding blade movement of the blade, essentially eliminates Z-axis chatter, which is prevalent in prior devices.

In the present invention, the cutting plane is generally vertical, in contrast to the prior art devices, in which the cutting plane is typically horizontal. This means that there are not required the long vibrating arms which were common in prior devices. The vibrating arm can essentially be as short as the cutting stroke and is thus very light weight. The vibrating unit is mounted on a preloaded linear bearing so that the vibrating unit can move freely in the vibrating, horizontal or X direction with no component of movement, by itself in either of the Y or Z axis directions. Very low wattage is required to move the vibrating element as compared to the higher levels of power required by prior vibrating microtomes.

The specimen to be sliced by the vibrating, sliding-blade microtome of the present invention is held in a specimen holder, as disclosed in detail in the prior Kong et al. U.S. Pat. No. 7,146,895. The combination of the specimen support structure and process, as described in the prior Kong et al. patent, together with the utilization of the vibrating, sliding-blade microtome of the present invention results in the preparation of extremely thin, sharply and accurately cut tissue specimens, particularly live tissue specimens. The slice viability, which is an important factor in the evaluation of a fresh, live tissue slice, is much greater than has been accomplishable using prior art devices. The live/dead cell ratio, which is a measurement of slice viability, is much greater in the present device, than has been the case when using traditional vibrating microtomes.

The method and device for cutting fresh tissue slices, in accordance with the present invention, overcomes a number of the significant limitations of the prior art devices. It is a substantial advance in the art.

BRIEF DESCRIPTION OF THE DRAWINGS

A full and complete understanding of the method and device for cutting fresh tissue slices, in accordance with the present invention may be had by referring to the detailed description of the preferred embodiment, as is set forth subsequently, and as illustrated in the accompanying drawings, in which.

DESCRIPTION OF THE PREFERRED EMBODIMENT

Figure 1:
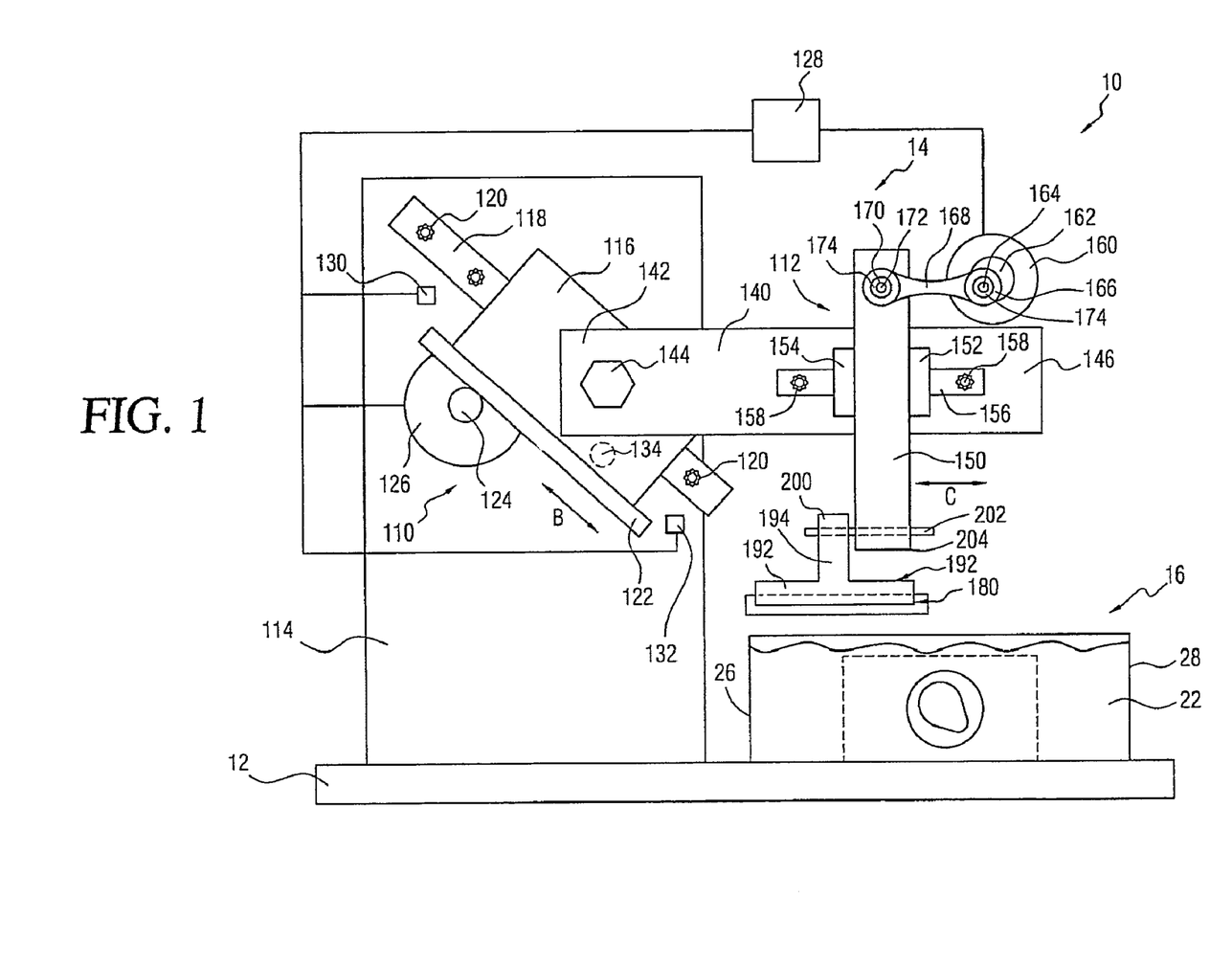
FIG. 1 is a front elevation view of a vibrating sliding-blade microtome in accordance with the present invention.

Referring initially to FIG. 1, there may be seen, generally at 10 a preferred embodiment of a vibrating sliding-blade microtome in accordance with the present invention. A generally planar base 12 supports a microtome assembly, generally at 14, and a specimen holding assembly, generally at 16. As will be discussed in detail shortly, the specimen holding assembly, generally at 16, is utilized to support and hold a tissue specimen so that a thin slice of the tissue can be cut from the specimen for further analysis. The specimen holding assembly, generally at 16, is similar, in overall structure and operation, to the specimen holding assembly described and depicted in the prior U.S. Pat. No. 7,146,895 in the names of the present applicants. As indicated above, the entire disclosure of that patent is expressly incorporated herein be reference.

Figure 2:
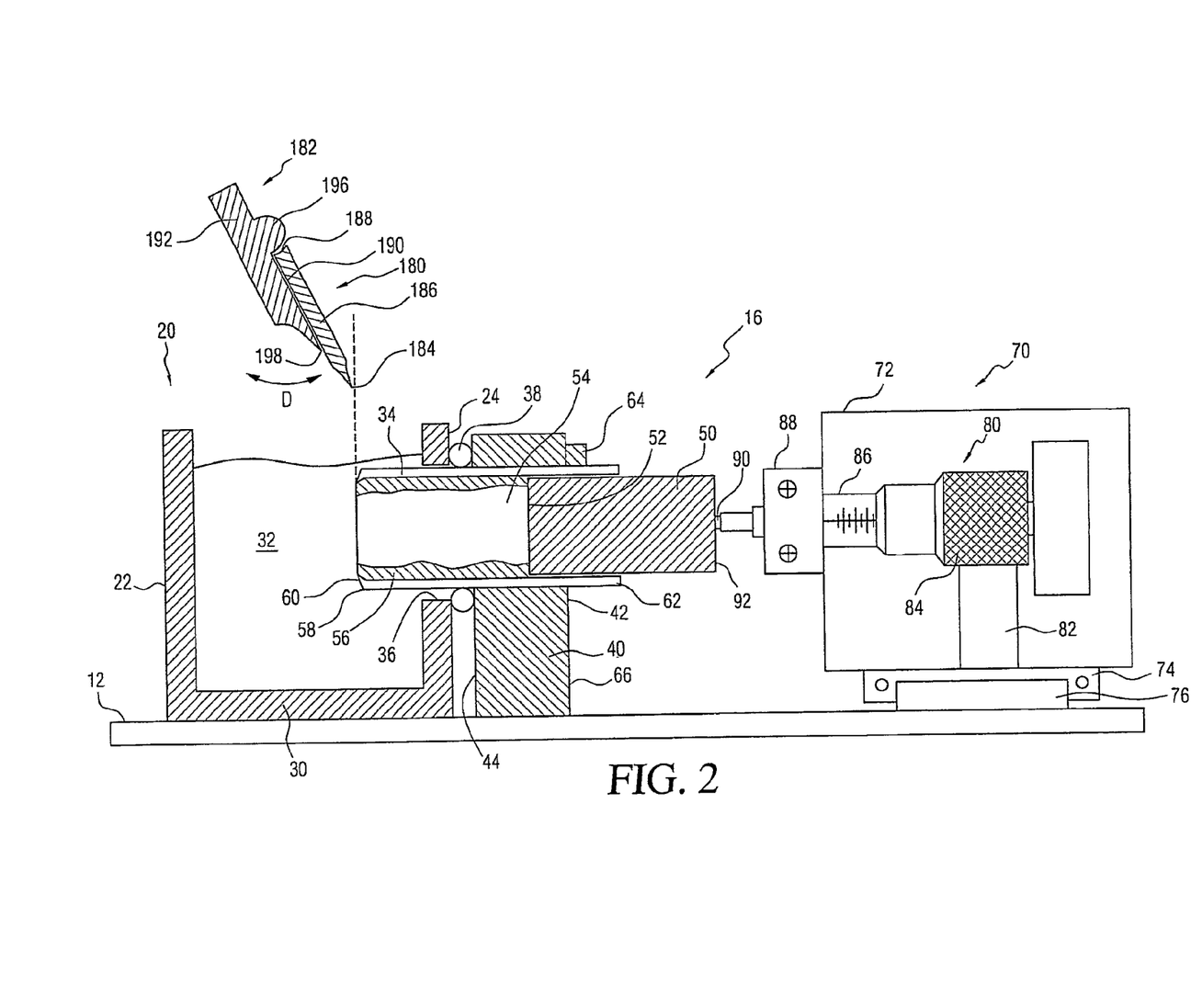
FIG. 2 is a side elevation view, partly in section, of the vibrating, sliding-blade microtome of FIG. 1 and showing a specimen being advanced in the specimen holder prior to its being sliced.

As may be seen by referring to FIG. 2, taken in conjunction with FIG. 1, the specimen holding assembly, generally at 16, includes a specimen receiving bath, generally at 20 which includes a bath front wall 22, a bath rear wall 24, left and right bath side walls 26 and 28, as seen in FIG. 1 and a bath bottom 30. The specimen receiving bath 20 thus is a fluid-tight receptacle into which can be placed a suitable saline solution 32 or any other fluid whose purpose will be to maintain the viability of a specimen slice that is deposited in the bath 20 by the action of the microtome assembly, generally at 14, as will be discussed subsequently.

Referring again to FIG. 2, a syringe tube 34 is insertable into an aperture 36 in the rear wall 24 of the specimen receiving bath, generally at 20. A resilient O-ring 38 surrounds the bath aperture 36 and will prevent leakage of the saline solution 32 or other liquid out of the specimen receiving bath 20 while the syringe tube 34 is inserted through the aperture 36. It will be apparent that the saline solution or other liquid solution 32 will be added to the bath only after the syringe tube 34 is in place and will be drained before the syringe tube 34 is removed. A syringe support base 40 is situated spaced behind, and generally parallel to the rear wall 24 of the specimen receiving bath. That base is provided with a base aperture 42 which is aligned with the bath rear wall aperture 36. As may also be seen in FIG. 2, the resilient O-ring 38 is sandwiched between the rear wall 24 of the specimen receiving bath 20 and a front wall 44 of the syringe support base 40.

The syringe tube 34 is a generally cylindrical tube that is sized to receive a cooperating syringe plunger 50. A leading face 52 of the syringe plunger 50 is adapted to have attached thereto a tissue specimen 54 which can be attached to the syringe leading face 52 by a suitable instantaneous adhesive or the like. Tissue specimen 54 will typically be encased in, or embedded in a low gel point agarose 56. As may be seen in FIG. 2, the syringe tube 34 has an outlet end 58 with a reduced diameter outlet lip 60 whose purpose is to provide some overcomable resistance to the passage of the tissue specimen 54 and its agarose encasement 56 out of the outlet end 58 of the syringe tube 34. Clearly, the reduced diameter outlet lip 60 does not provide a complete barrier to the passage of the tissue specimen 54 and its embedding agarose 56 out of the syringe tube outlet end 58.

The syringe tube 34 is also structured with an inlet end 62 which, in the present invention is sized to slidingly receive the syringe plunger 50. A stop 64 is attached to the syringe tube 34 intermediate the syringe tube ends 58 and 62 respectively. Stop 64 is positioned so that it will abut a rear wall 66 of the syringe support base 40. Stop 64 thus functions to ensure that the syringe tube 34 will extend into the saline solution 32 or other liquid in the specimen receiving bath 20 to a pre-determined, repeatable depth or position. This will aid in the aligning of the vibrating sliding-blade microtome with the outlet end 58 of the syringe tube 34.

Figure 3:
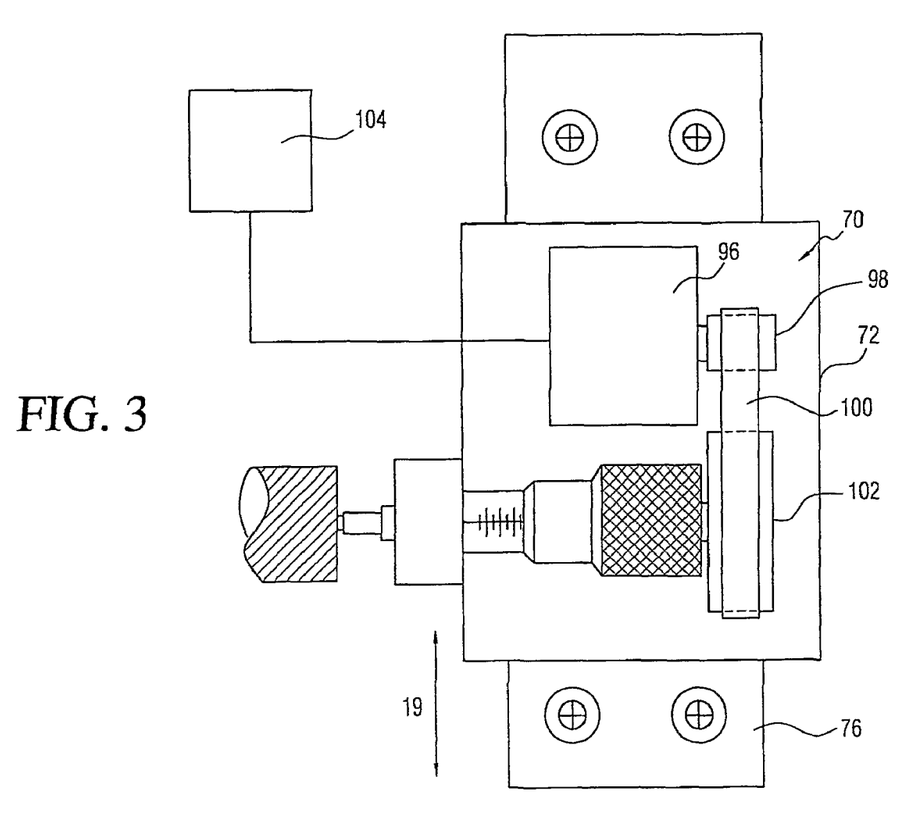
FIG. 3 is a top plan view of a portion of the vibrating, sliding-blade microtome of the present invention and showing a micrometer drive assembly.

A micrometer drive, generally at 70, is, as may be seen in FIGS. 2 and 3, situated in a micrometer drive housing, generally at 72. The micrometer drive housing 72 is, in turn, secured atop a micrometer drive housing carrier plate 74 which is slidable, in the directions indicated by the arrow A in FIG. 3, along a micrometer drive housing linear slide 76 which is, in turn, secured to the base 12 by any suitable expedient. A micrometer 80 is situated atop a support pedestal 82 in the micrometer drive housing 72 and has a micrometer body 84 which carries a micrometer plunger 86 which passes through the micrometer drive housing 72 and through a mounting plate 88 attached to the micrometer drive housing 72. A free end 90 of the micrometer plunger 86 is engagable with a syringe plunger outer face 92.

A micrometer drive motor 96 is situated in the micrometer drive housing 72 and is preferably provided as a suitable electric stepper motor. Micrometer drive motor 96 has a micrometer motor drive gear 98 which supports a micrometer drive belt 100 that extends from the micrometer motor drive gear 98 to a micrometer drive gear 102. Both of these drive gears 98 and 102 are externally toothed and engage interior teeth or cogs on the drive belt 100. The micrometer drive motor 96 is very precisely controlled by a micrometer motor control 104. That control can be actuated to rotate the micrometer drive stepper motor 96 a finite amount so that the micrometer plunger 86, and specifically its free end 90 will engage the syringe plunger 50 and can advance it in the syringe tube 34 a defined amount. Such a defined amount of forward travel of the syringe plunger 50 will extrude a set length of the specimen 54 and embedding agarose 56 out of the reduced diameter outlet lip 60 of the syringe tube 34 so that it can be sliced off by the vibrating sliding-blade microtome and deposited in the saline solution 32 or the other suitable solution in the specimen receiving bath 20 where it can be removed for further processing. When it is necessary to remove the syringe plunger 50 out of the rear, inlet end 62 of the syringe tube 34, the micrometer plunger 86 and its free end 90 can be retracted toward the micrometer drive housing 72 by reversal of the micrometer drive motor 96. Once the micrometer plunger 86 has been so retracted, the micrometer drive housing 72 can be slid laterally on the micrometer drive housing slide 76. If desired, suitable clamps, which are not specifically shown, can be used to hold the micrometer drive housing 72 in its operational position, and can be loosened to allow it to slide laterally to its non-use position.

Referring now again to FIG. 1, the vibrating sliding-blade microtome assembly, generally at 14, in accordance with the present invention, will be described in detail. It will be quite evident to those of skill in the art that the purpose of the microtome is to slice thin uniform viable tissue samples from the tissue specimen 54 embedded in the low gel point agarose 56 and extruded or forced out of the syringe outlet end 58 and restricted by the reduced diameter outlet lip 60. The incremental advance of that tissue specimen 54 is accomplished by operation of the micrometer stepper drive motor 96, under the control of the micrometer motor controller 104. The proper embedding of the tissue specimen 54 in the low gel point agarose 56 and the cooperation of the syringe tube 34, the reduced diameter outlet tip 60 and the provision and control of the micrometer stepper drive motor 96 will set up the tissue for its being sliced. However, if the microtome blade is not able to perform an effective cut, the accurate tissue specimen set-up and positioning is of no consequence. In the prior devices, as discussed above, the microtome blade has tended to chatter and to bend or deflect, has tended to compress the tissue instead of cutting it and has generally failed to provide very thin, reproducible tissue specimen slices of live or soft tissue. The vibrating sliding-blade microtome of the subject invention overcomes those limitations.

As may be seen most clearly in FIG. 1, the vibrating sliding-blade microtome, generally at 14, is comprised essentially of two distinct yet interacting components. The first of these is a diagonal sliding component, generally at 110. The second is a horizontal vibrating component, generally at 112. While the two components have separate features, they combine to much more effectively slice the tissue specimens 54.

A support column 114 extends upwardly from the base 12 of the vibrating sliding-blade microtome, generally at 10. This column 114 is depicted in FIG. 1 as being generally rectangular but need not have any specific shape so long as it has sufficient structural rigidity to support the two cooperating components 110 and 112. A diagonal slide platform 116 is supported for diagonal movement along a diagonal slide rail 118 which is, in turn, secured to the support column 114 by suitable fasteners, such as the fastener bolts 120 depicted schematically in FIG. 1. It will be understood that the diagonal slide platform 116 and the diagonal slide rail 118 will preferably have friction reducing components, such as linear bearings, low friction slide surfaces or the like so that the platform 116 will be able to slide easily along the slide rail 118. It will also be understood that the angle of inclination of the diagonal slide rail 118, with respect to a horizontal line, could be varied such as, for example, by providing arcuate slots in the support column 114 and having the fastener bolts 120 be received in those arcuate slots. This angle of inclination is preferably between 20° and 80°. Other angle adjusting expedients are within the purview of the subject invention.

A gear tooth rack 122 is attached to the lower edge of the diagonal slide platform 116 and is in gear mesh with a cooperating drive pinion 124. That drive pinion is driven by a diagonal slide platform drive motor 126 which is preferably a stepper motor whose revolutions are accurally controllable by a slide platform drive motor controller 128. A pair of Hall-Effect sensors 130, 132 are situated adjacent first and second ends of the diagonal slide rail 118. A suitable magnet 134 is affixed to the diagonal slide platform 116. In operation, readings from the two Hall Effect sensors 130, 132 are sent to the diagonal slide platform drive motor controller 128 and are usable to very accurately position the diagonal slide platform 116. It will be understood that other similar control schemes could be used to accurately determine and control the position of the diagonal slide platform 116 along the diagonal slide rail 118. It is important the platform 116 be capable of sliding in a diagonal direction, with respect to X and Y axes, as indicated by arrow B in FIG. 1, and that its positioning and magnitude of slide travel be capable of being accurately controlled.

A support arm 140 is secured, at a first, attached end 142, to the diagonal slide platform 116 by a suitable fastener, such as a bolt 144. It will be understood that the bolt 144 is a schematic representation of any suitable fastening arrangement that could be used to attach the support arm 140 to the diagonal slide platform 116. Since it is preferable that the support arm 140 be maintained generally horizontally, the fastening arrangement 144 could be adjustable so that the support arm 140 would remain horizontal with varying inclinations of the diagonal slide rail 118. A second, free end 146 of the support arm 140 extends, in a cantilever fashion, over the specimen holding assembly, generally at 16. It will be understood that the support arm 140 is depicted in the somewhat schematic illustration of the subject invention in FIG. 1, as a generally rectangular member. In actuality, the support arm 140 could take any number of shapes so long as it has sufficient structural rigidity to accomplish its intended task, as will now be discussed.

A vibrating blade support 150 is carried by a pair of spaced blade support carriers 152, 154 which are slidable horizontally along a blade support rail 156. That blade support rail 156 is, in turn, bolted or otherwise fastened to the support arm 140 intermediate its ends 142 and 146, as indicated schematically by bolts 158. As was discussed in connection with the diagonal slide platform 116 and the diagonal slide rail 118, the blade support carriers 152 and 154, which may be a unified blade support carriage, and the blade support rail 156 may be provided with friction reducing elements, such as linear bearings, allow friction slide or other friction reducing components and the like. The result is that the vibrating blade support 150 is supported so that it will move or reciprocate very freely and easily in the horizontal or X-axis direction, as indicated by arrow C in FIG. 1. A vibrating blade drive motor 160 is situated atop the support arm 140 generally adjacent the free, unsupported second end 146 of that support arm 140. That vibrating blade drive motor 160 is typically also an electric motor and is controlled by the same motor controller 128 which also controls the diagonal slide platform drive motor 126. Coordination between the two motors 126 and 160 is thus assured through the provision of the common controller 128. A drive wheel 162 is driven by this motor 160 and is provided with an eccentrically situated drive pin 164. That drive pin is received in a first end 166 of a resilient or spring steel connector link 168. A second end 170 of this connector link 168 is carried by a blade support drive pin 172. As indicated schematically in FIG. 1 both ends 166 and 170 of the resilient or spring steel connector link 168 may be provided with suitable bearing assemblies, generally at 174, which bearing assemblies aid in the support and connection of the connector link 168.

Actuation of the vibrating blade drive motor 160 will cause the drive wheel 162 to rotate at a relatively high rate of speed. The eccentric location of the drive pin 164 will cause the connector link 168 to reciprocate. This reciprocatory motion of the connector link 168 is translated into a horizontal vibration of the vibrating blade support 150 in the direction indicated by arrow C in FIG. 1.

A cutting blade, generally at 180, is attached to a blade holder, generally at 182, as seen in FIG. 1, and as is also seen in greater detail in FIG. 2. The cutting blade 180 has an elongated blade edge 184 and a blade body 186. Typically, the cutting blade 180 is one half of a double-edged razor blade. The blade body 186 has a top edge 188 and a blade side 190. The blade holder 182 is generally in the shape of an inverted T, as seen in FIG. 1 and includes a blade holder bar 192 which is attached, generally at its mid-point to a blade holder leg 194. As seen in FIG. 2, the blade holder bar 192 has a horizontal ridge 196 which acts as an abutment which will be engaged by the upper edge 188 of the blade body 186. The blade cutting edge 184 extends below a lower edge 198 of the blade holder bar 192. In use, the cutting blade 180 is attachable to the blade holder bar 192 by the use of a suitable adhesive which will be applied to the entire length of the blade holder bar 192, below the ridge 196 thereof and to the cutting blade side 190. The cutting blade 180 will be adhesively attached to the blade holder bar 192 so that its cutting edge 184 protrudes below the blade holder bar lower edge 198 by a distance of approximately 1 mm. This support of the cutting blade 180 by the cutting blade holder 182 prevents the cutting blade 180 from bending or flexing, as typically happens with blades attached to holders only in several spaced locations.

Referring again to FIG. 1, an upper end 200 of the blade holder leg 194 is pivotally supported by a blade holder support rod 202. That blade holder support rod 202 is situated adjacent a lower end 204 of the vibrating blade support 150. A suitable securement assembly, such as a clamping screw, a set screw, or the like is provided, either at the juncture of the blade holder leg 194 and the rod 202, or at the juncture of the rod 202 and the lower end 204 of the vibrating blade support 150 so that an angle of inclination of the cutting blade 180 can be varied over an arc D, with respect to the end of the specimen to be sliced, as depicted in FIG. 2.

In operation of the vibrating, sliding-blade microtome, in accordance with the present invention, a tissue specimen 54 is secured to the syringe leading face 52 and is embedded in a suitable low gel point agarose 56. The syringe plunger 50 is inserted into the syringe barrel or tube 34, from the inlet end 62. The now assembled syringe is inserted into the aligned apertures of the bath rear wall 24 and of the syringe support base 40. Once this has been done, the specimen receiving bath 20 can be filled with a suitable saline solution 32 or other similar sample receiving medium. The micrometer drive 70, which had been slid out of the way or out of alignment with the aligned apertures 36 and 42, is now slid along the micrometer drive housing linear slide 76 until the micrometer plunger 86, and specifically its free end 90, is aligned with the syringe plunger outer face 92. At this point, the micrometer drive motor 96 with its controller 104, which is in connection with the controller 128 for the diagonal sliding platform drive motor 126 and the vibrating blade drive motor 160, is actuated to advance the tissue specimen 54 out through the reduced diameter outlet lip 60 of the syringe tube 34.

The diagonal slide platform 116 is caused to move down and to the right, as seen in FIG. 1, in the direction of the arrow B. At the same time, the cutting blade 180 is caused to vibrate horizontally in the direction of the arrow C. The compound sliding and vibrating motion of the cutting blade 180 is effective to slice a first tissue slice off the tissue specimen 54. That first slice will typically be discarded because its outer surface, the surface not newly formed by the blade 180, will not be even. Subsequent slices, which are obtained by the steps of advancing the syringe plunger 50 and by the vibrating and diagonally sliding movement of the cutting blade 180, are much more uniform in thickness and can be retrieved from the saline solution 32 for further processing.

In the vibrating and sliding-blade microtome in accordance with the present invention, the cycle time is substantially reduced from that which is possible using only a vibrating blade microtome. In addition, the slice thickness is much more uniform than has been possible in prior devices. The Hall Effect sensors 130 and 132 limit the travel of the diagonal slide platform 116 so that there is no unnecessary platform travel. The short vibrating strokes imparted to the vibrating blade support 150 are very efficient and again reduce specimen cutting or slicing time. The cutting edge 184 of the cutting blade 180 moves in a plane, indicated by dashed lines in FIG. 2, which is parallel to the plane of the decreased diameter lip 60 of the syringe tube 34, the specimen slices are thus sliced clearly, quickly and with an accurately and controllable thickness.

Figure 4:
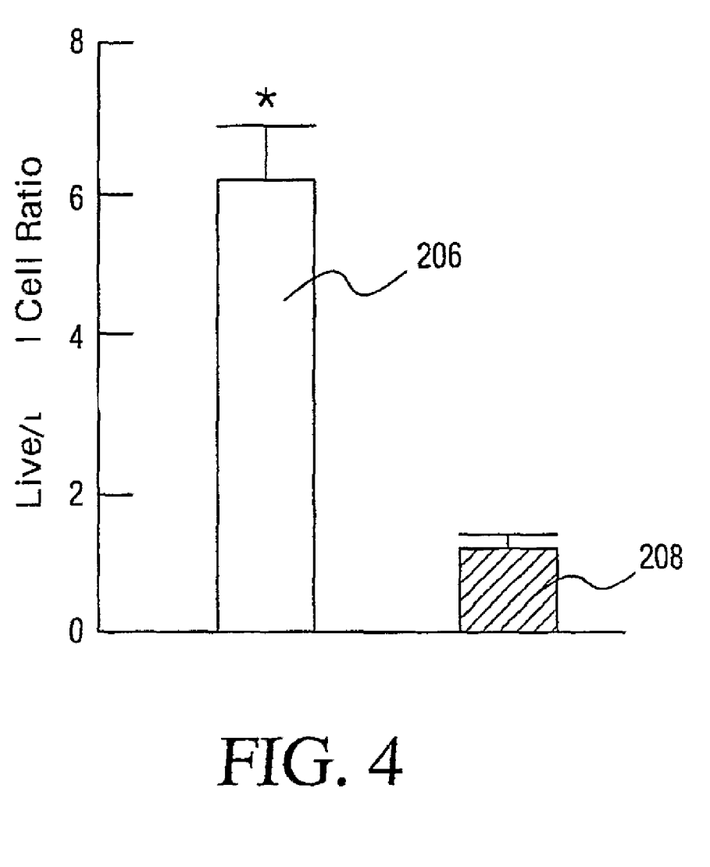
FIG. 4 is a bar graph depiction of live/dead cell ratios obtainable by use of the present invention and compared with the results obtainable using a prior art device.

One effective measure of the viability of a specimen slice is a ratio of live to dead cells. The higher the ratio; i.e. the greater number of live cells there are for each dead cell, is an excellent measure of slice viability. As may be seen in FIG. 4, the slice viability 206 of slices prepared using the vibrating, sliding-blade microtome in accordance with the present invention, as a ratio of live/dead cells, is much better than a ratio 208 obtained using a prior vibrating microtome. The vibrating, sliding-blade microtome, in accordance with the present invention is thus clearly far superior to the products which are currently available.

While a preferred embodiment of a method and device for cutting fresh tissue slices, in accordance with the present invention has been set forth fully and completely hereinabove, it will be apparent to one of skill in the art that various changes in, for example, the nature of the specimen slice receiving bath, the specifics of the several drive motors and their controllers, the specific adhesive used to secure the cutting blade to the blade holder, and the like could be made without departing from the true spirit and scope of the present invention, which is accordingly to be limited only by the following claims.

What is claimed is:

1. A method for cutting a slice of a specimen tissue comprising the steps of:
providing a base and a specimen holder attachable to said base, said specimen holder including:
a diagonal slide carriage on said base, said diagonal slide carriage being supported for movement diagonally with respect to said specimen holder, wherein the diagonal slide carriage includes a movable diagonal slide platform and a diagonal slide rail and further includes a diagonal slide platform drive motor;
a support arm on said diagonal slide carriage and movable with said diagonal slide carriage;
a vibrating blade support on said support arm and movable horizontally with respect to said specimen holder; and
a specimen cutting blade on said vibrating blade support, said specimen cutting blade being movable in a compound diagonal and vibrating movement with respect to said specimen holder;
attaching a specimen to be sliced to said specimen holder;
supporting said specimen cutting blade for horizontal vibrating movement and for diagonal sliding movement with respect to said specimen holder;
extending a free end of said specimen from said specimen holder; and
severing a slice of said specimen by vibrating and diagonally sliding said specimen cutting blade with respect to said specimen.

2. The method of claim 1 further including providing a vibrating blade drive motor and using said vibrating blade drive motor for effecting said horizontal vibrating movement of said specimen cutting blade.

3. A device for cutting specimen slices comprising:
a base;
a specimen holder attachable to said base;
a diagonal slide carriage on said base, said diagonal slide carriage being supported for movement diagonally with respect to said specimen holder, wherein the diagonal slide carriage includes a movable diagonal slide platform and a diagonal slide rail and further includes a diagonal slide platform drive motor;
a support arm on said diagonal slide carriage and movable with said diagonal slide carriage;
a vibrating blade support on said support arm and movable horizontally with respect to said specimen holder; and
a cutting blade on said vibrating blade support, said cutting blade being movable in a compound diagonal and vibrating movement with respect to said specimen holder.

4. The device of claim 3 further including a rack on said diagonal slide platform and a coacting pinion on said diagonal slide platform drive motor.

5. The device of claim 3 further including a motor controller for said diagonal slide platform drive motor.

6. The device of claim 5 further including spaced Hall Effect sensors on said base and a magnet on said diagonal slide platform, said Hall Effect sensors being connected to said motor controller.

7. The device of claim 3 further including a vibrating support drive motor on said support arm.

8. The device of claim 7 further including an eccentric drive on said vibrating blade support drive motor.

9. The device of claim 7 further including a connecting link between said vibrating blade support drive motor eccentric drive and said vibrating blade support.

10. The device of claim 9 wherein said connecting link is spring steel.

11. The device of claim 3 further including a vibrating blade support carriage connecting said vibrating blade support and said support arm.

12. The device of claim 11 further including a vibrating blade support rail secured to said support arm and supporting said vibrating blade support carriage.

13. The device of claim 3 further including a blade holder on said vibrating blade support.

14. The device of claim 13 further including a horizontal ridge on said blade holder and adapted to define a location for the attachment of a cutting blade to said blade holder.

* * * * *